United States Patent
Konesky et al.

(10) Patent No.: US 9,492,219 B2
(45) Date of Patent: **\*Nov. 15, 2016**

(54) SYSTEMS AND METHODS OF DISCRIMINATING BETWEEN ARGON AND HELIUM GASES FOR ENHANCED SAFETY OF MEDICAL DEVICES

(71) Applicant: Bovie Medical Corporation, Clearwater, FL (US)

(72) Inventors: Gregory A. Konesky, Hampton Bays, NY (US); Borislav S. Simeonov, St. Petersburg, FL (US)

(73) Assignee: Bovie Medical Corporation, Clearwater, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/811,019

(22) Filed: Jul. 28, 2015

(65) Prior Publication Data

US 2015/0335374 A1    Nov. 26, 2015

Related U.S. Application Data

(63) Continuation of application No. 13/802,227, filed on Mar. 13, 2013, now Pat. No. 9,095,333.

(60) Provisional application No. 61/667,213, filed on Jul. 2, 2012, provisional application No. 61/716,688, filed on Oct. 22, 2012.

(51) Int. Cl.
  *A61B 18/04* (2006.01)
  *A61B 18/10* (2006.01)
  *A61B 18/12* (2006.01)

(52) U.S. Cl.
  CPC ............. *A61B 18/042* (2013.01); *A61B 18/10* (2013.01); *A61B 18/1233* (2013.01); *A61B 2018/122* (2013.01)

(58) Field of Classification Search
  USPC .................................................. 606/20–52
  See application file for complete search history.

(56) References Cited

U.S. PATENT DOCUMENTS

| 7,654,975 B2 | 2/2010 | Mantell |
| 2005/0075630 A1 | 4/2005 | Truckai et al. |
| 2007/0028669 A1 | 2/2007 | Brewster |

FOREIGN PATENT DOCUMENTS

| EP | 0878263 | 11/1998 |
| EP | 1764057 | 3/2007 |

(Continued)

OTHER PUBLICATIONS

European Search Report for European Application No. 13172979.0; dated Oct. 11, 2013; six (6) pages.

(Continued)

*Primary Examiner* — Paula J Stice
(74) *Attorney, Agent, or Firm* — Gerald E. Hespos; Michael J. Porco; Matthew T. Hespos

(57) ABSTRACT

Systems and methods for discriminating between various gases, e.g., argon and helium, for enhanced safety of medical devices are provided. The present disclosure may take the form of a dedicated-use embodiment where a specific gas, helium for example, is expected, and an enabling or "Go" signal is issued when that gas is detected, or an inhibitory or "No-Go" signal when a gas is present that is not identified as helium. Alternately, a control line or input command can be used to select between helium and argon as the expected gas and then issue the appropriate "Go/No-Go" signal, depending on which gas is identified.

13 Claims, 13 Drawing Sheets

(56) References Cited

FOREIGN PATENT DOCUMENTS

| | | |
|---|---|---|
| EP | 2263728 | 12/2010 |
| WO | 2004/096315 | 11/2004 |

OTHER PUBLICATIONS

Kirschner, Jared; Surface Acoustic Wave Sensors (SAWS): Design for Application, Microelectromechanical Systems, Dec. 6, 2010; pp. 1-11.

Gas discrimination by acoustic absorption

Paschen curves for various gases.

Differential breakdown voltage timing for helium and argon

Differential breakdown volatges for helium and argon using a sine wave.

Ionization discharge timing to discriminate gases.

Single band pass emission spectrum discrimination.

Dual band pass emission spectra discrimination

Illustration of a resonant condition

Illustration of a non-resonant condition

Single transducer resonator with reflective surface.

Change in transducer current during resonance.

Two transducers with resonator

Resonant conditions with sweeping frequencies for different gases.

System to measure the wavelength-dependent phase difference

Time-of-flight measurement system

SYSTEMS AND METHODS OF DISCRIMINATING BETWEEN ARGON AND HELIUM GASES FOR ENHANCED SAFETY OF MEDICAL DEVICES

PRIORITY

This application claims priority on U.S. Provisional Patent Appl. No. 61/667,213, filed Jul. 2, 2012, and U.S. Provisional Patent Appl. No. 61/716,688, filed Oct. 22, 2012, the contents of which are hereby incorporated by reference in their entireties.

BACKGROUND

1. Field

The present disclosure relates generally to electrosurgery and electrosurgical systems and apparatuses, and more particularly, to systems and methods for discriminating between various gases, e.g., argon and helium, for enhanced safety of medical devices.

2. Description of the Related Art

Medical devices which produce a plasma, or ionized gas, utilize an inert carrier gas such as helium or argon. Devices which use helium typically produce a "cold plasma" beam which is ideal for sterilization and hemostasis (i.e., stop bleeding), although it can be used at higher power for tissue ablation. The effects are generally highly localized, and often, this device is used without a return pad.

Medical plasma devices which use argon typically produce a hotter plasma beam which can also be used for hemostasis and tissue ablation, but the effects are more widespread, with greater collateral damage of surrounding tissue than devices that use helium. A return pad is usually required for argon-based devices, and higher plasma voltage and current are needed as compared to helium-based devices.

Both helium and argon are colorless, odorless, non-toxic gases. Medical plasma devices designed to operate with helium perform poorly with argon at low powers, and may produce a dangerous and unexpectedly hot beam at high power settings and may also damage the device. Similarly, devices designed to operate with argon can also be damaged if helium is used instead, due to the lower ionization voltage of helium.

Mass spectrometry has been used to identify both helium and argon by their atomic mass, but these devices are neither simple nor inexpensive. Therefore, it would be useful to have a simple and inexpensive device to discriminate between helium and argon, and inhibit operation of the appropriate plasma medical device if the wrong gas supply is connected.

SUMMARY

Systems and methods for discriminating between various gases, e.g., argon and helium, for enhanced safety of medical devices are provided. The present disclosure may take the form of a dedicated-use embodiment where a specific gas, helium for example, is expected, and an enabling or "Go" signal is issued when that gas is detected, or an inhibitory or "No-Go" signal when a gas is present that is not identified as helium. Alternately, a control line or input command can be used to select between helium and argon as the expected gas and then issue the appropriate "Go/No-Go" signal, depending on which gas is identified.

The systems and methods of the present disclosure may be employed where mixtures of gases are used, for example, a blend of both helium and argon, or helium containing oxygen, or other gas combinations. In one embodiment, the gas discriminating systems of the present disclosure produces an internal test result signal that is associated with a specific gas combination ratio that is stored for subsequent comparisons. This internal test result signal can then be compared to a measured value and a "Go/No Go" signal is then issued if the expected gas combination is present or not.

The systems and methods of the present disclosure may also be employed to verify the purity of the gas used, again, depending on the value of an internal test result signal, and issue a "Go/No Go" if the gas has an acceptable purity level, or not.

The system can be implemented as an integral part of a newly constructed medical plasma device, for example, an electrosurgical generator, or it can be implemented as an external add-on device to provide enhanced safety to a pre-existing medical plasma device. In the latter example, a "Go/No-Go" signal line would connect to the pre-existing system to enable operation if the expected gas is present and inhibit it otherwise.

According to one aspect of the present disclosure, an apparatus for use with a medical device includes at least one gas input configured to receive a gas; a gas discriminator coupled to the at least one gas input and configured to determine a type of the gas, the gas discriminator further configured to generate a signal indicative of the determined gas type; and a controller configured to receive the gas type signal, compare the gas type to an expected gas type and generate a control signal to enable or disable the medical device based on the comparison.

In another aspect, an electrosurgical generator for performing electrosurgery on a surgical site of a patient, the electrosurgical generator is provided including an electrical power source to supply electrosurgical energy to an electrode of a hand-held plasma generator; and at least one gas input configured to receive a gas; a gas discriminator coupled to the at least one gas input and configured to determine a type of the gas, the gas discriminator further configured to generate a signal indicative of the determined gas type; and a controller configured to receive the gas type signal, compare the gas type to an expected gas type and generate a control signal to enable or disable the electrical power source based on the comparison.

In a further aspect of the present disclosure, an electrosurgical system for performing electrosurgery on a surgical site of a patient includes an electrosurgical generator coupled to an electrical power source to supply power for the electrosurgical system; a plasma generator including a noble gas conduit and an electrode disposed with the noble gas conduit, the electrode operatively coupled to the electrosurgical generator to selectively receive electrical energy therefrom such that the electrode at least partially ionizes a carrier gas feed to the noble gas conduit to create a plasma discharge; and at least one gas input configured to receive a gas; a gas discriminator including at least one gas input configured to receive the noble gas and to determine a type of the gas, the gas discriminator further configured to generate a signal indicative of the determined gas type, wherein the gas discriminator further includes a controller configured to receive the gas type signal, compare the gas type to an expected gas type and generate a control signal to enable or disable the system on the comparison.

BRIEF DESCRIPTION OF THE DRAWINGS

The above and other aspects, features, and advantages of the present disclosure will become more apparent in light of the following detailed description when taken in conjunction with the accompanying drawings in which.

Figure 1:
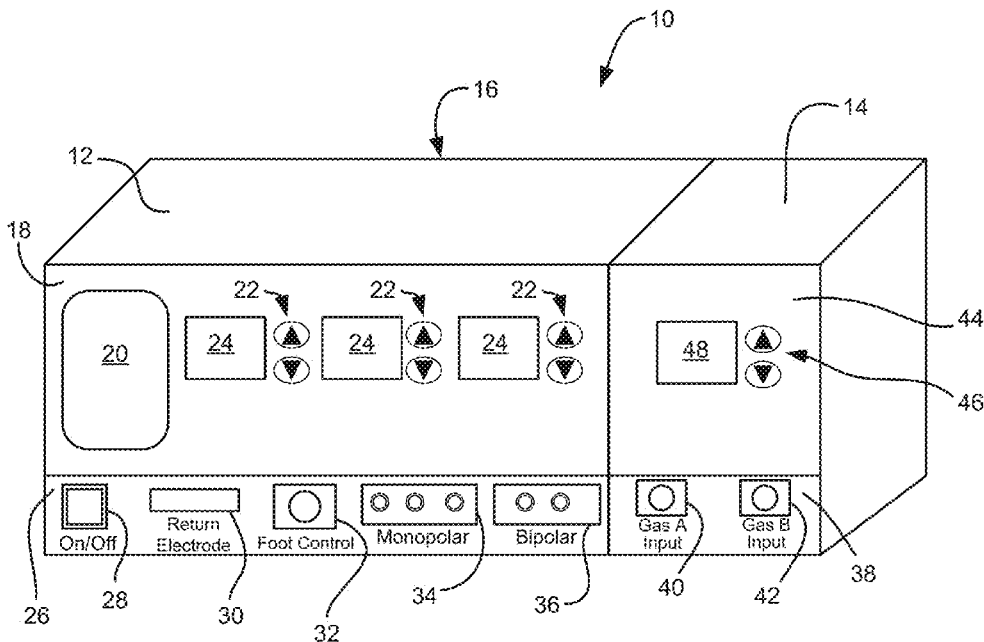
FIG. 1 is an illustration of an exemplary medical plasma apparatus in accordance with an embodiment of the present disclosure.

It should be understood that the drawing(s) is for purposes of illustrating the concepts of the disclosure and is not necessarily the only possible configuration for illustrating the disclosure.

DETAILED DESCRIPTION

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

Systems and methods for discriminating between various gases, e.g., argon and helium, for enhanced safety of medical devices are provided. The present disclosure may take the form of a dedicated-use embodiment where a specific gas, helium for example, is expected, and an enabling or "Go" signal is issued when that gas is detected, or an inhibitory or "No-Go" signal when a gas is present that is not identified as helium. Alternately, a control line or input command can be used to select between helium and argon as the expected gas and then issue the appropriate "Go/No-Go" signal, depending on which gas is identified.

The system can be implemented as an integral part of a newly constructed medical plasma device, or it can be implemented as an external add-on device to provide enhanced safety to a pre-existing medical plasma device. In the latter example, a "Go/No-Go" signal line would connect to the pre-existing system to enable operation if the expected gas is present and inhibit it otherwise.

Referring to FIG. 1, an exemplary medical plasma apparatus 10 in accordance with the present disclosure is illustrated. In one embodiment, the apparatus 10 includes a high frequency electrosurgical generator 12 and gas discriminator 14 contained in a single housing 16. Exemplary electrosurgical generators are disclosed in commonly owned U.S. Pat. No. 8,100,897 and U.S. patent application Ser. No. 12/761,520, the contents of which are incorporated by reference. Electrosurgery is a term used to describe the passage of high-frequency (i.e., radio frequency (RF)) electrical current through tissue to create a desired clinical tissue effect. The electrosurgical generator 12 includes a front panel face 18 which includes an input section 20, e.g. a touchscreen, for entering commends and data into the generator and various level controls 22 with corresponding indicators 24. The electrosurgical generator 12 further includes a receptacle section 26 which includes a On/Off switch 28, a return electrode receptacle 30, a monopolar footswitching receptacle 32, monopolar handswitching receptacle 34 and a bipolar handswitching receptacle 36. The gas discriminator 14 includes a gas receptacle portion 38 which further includes a Gas A input receptacle 40 and a Gas B input receptacle 42. The gas discriminator 14 further includes a user interface portion 44 including selector switch 46, for example, to select the type of gas being input, and a display 48. As will be described below in further detail, the gas discriminator 14 determines whether the expected type of gas is being input and provides the appropriate "Go/No-Go" signal to the electrosurgical generator 12.

It is to be appreciated that although FIG. 1 shows the generator 12 and gas discriminator 14 housed in a single housing 16, gas discriminator 14 may be provided as a separate, external device which interfaces with conventional electrosurgical generators.

Figure 2:
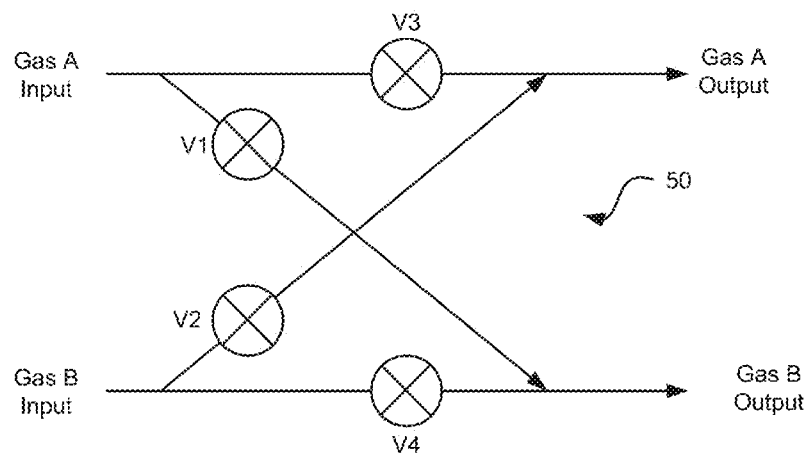
FIG. 2 is an illustration of a gas cross-over network in accordance with an embodiment of the present disclosure.

An adaptive system can be implemented where both helium and argon are used in the same system and potential exists for these gases to be misconnected to the medical plasma device. As shown in FIG. 2, a cross-over network 50, consisting of valves V1 and V2 can be used to redirect Gas A Input to Gas B Output and vice versa, with valves V3 and V4 closed to prevent backflow, if a misconnection is identified. On the other hand, if a correct connection is identified (i.e. helium gas is identified in the helium gas input, and similarly for argon), then cross-over valves V1 and V2 are closed and direct flow-through valves V3 and V4 are opened. Not shown is the controller logic that would operate the valves V1 through V4 in their appropriate combinations, based on a "Go/No-Go" signal from one of the detection techniques described below.

Various techniques of discriminating helium from argon are contemplated to be within the scope of the present disclosure. The first approach relies on the high coefficient of absorption of ultrasonic frequencies by helium that is not exhibited by argon. A second technique is described which utilizes the difference in ionization potential between helium and argon. A third approach employs the different emission spectra of ionized helium and argon. A further technique employs the differential velocity of propagation between gases. It is to be appreciated that each of the various techniques to be described below may be embodied in gas discriminator 14, as part of the medical apparatus 10 or as an external device.

I. Discrimination by Acoustic Absorption:

Helium has unique physical properties such as low density and high thermal conductivity. These properties lead to strong absorption of acoustical signals, particularly in the ultrasonic region. Neither argon nor air shows this same strong acoustical absorption feature. This property is used to realize a simple and inexpensive means of discriminating between helium and argon. A system 100 employing discrimination by acoustic absorption is shown in FIG. 3.

Figure 3:
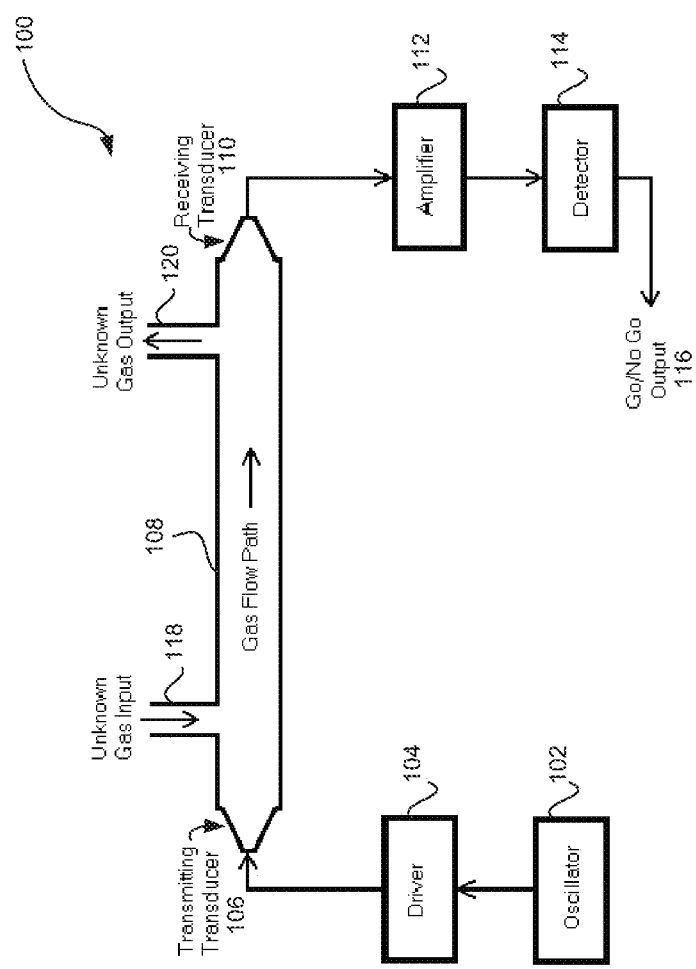
FIG. 3 is a diagram of a gas discrimination system employing acoustic absorption in accordance with an embodiment of the present disclosure.

As illustrated in FIG. 3, an ultrasonic oscillator 102 feeds a driver stage 104 which then operates a transmitting ultrasonic piezoelectric transducer 106. Sound waves travel down a tube 108 to a receiving ultrasonic transducer 110 whose output is amplified via amplifier 112 and detected via detector 114 to provide a "Go/No-Go" signal 116 to enable or disable, respectively, the medical device. The tube 108 through which the ultrasonic waves travel also have side tubes to admit the unknown gas, e.g., gas input 118 and gas output 120.

As an example, an ultrasonic drive signal is presented to the transmitting transducer 106, via the driver 104, at approximately 39 kHz, so that a received signal at the receiver transducer 110 is about 2.5 Vpp when either air or argon is used. When helium is admitted into one of the side tubes 118 and flushes out the air or argon, the received signal strength drops to approximately 25 mVpp, or about a factor of 100 decrease in signal strength. The "Go/No-Go" signal 116 is generated by the detector 114 based on the received signal strength. In one embodiment, the detector 114 is configured with a predetermined threshold to determine if the gas is air/argon or helium. For example, when the received signal strength is above the predetermined threshold, the gas is determined to be air/argon; alternatively, if the received signal strength is below the predetermined threshold, the gas is determined to be helium. In another embodiment, the detector 114 determines if the received signal strength is within a predetermined range for each type of gas.

Figure 4:
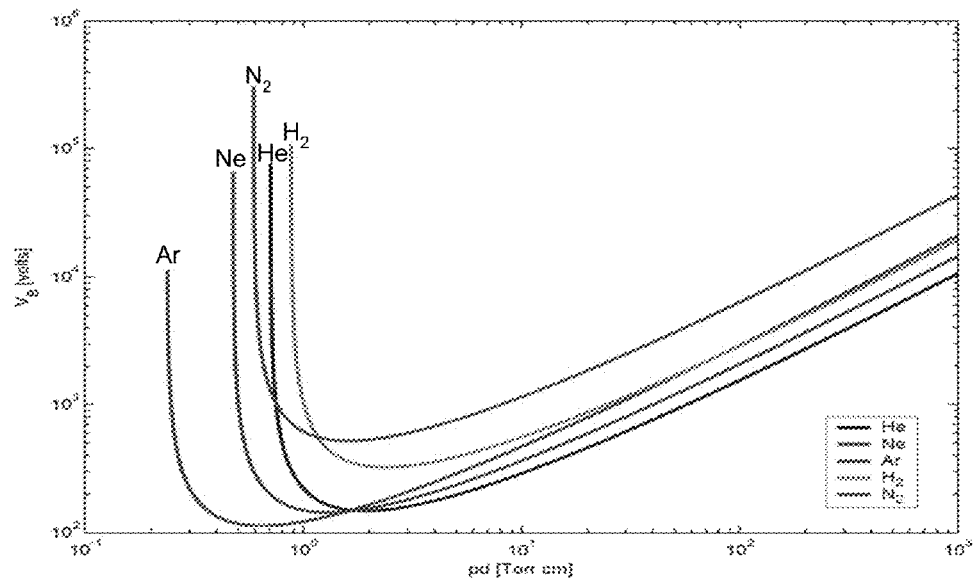
FIG. 4 is an illustration of Paschen curves for various gases.

II. Discrimination by Ionization Timing:

Helium has the highest ionization potential of any gas at 24.6 eV. It is considerably higher than that of argon at approximately 15.8 eV, and the constituents of air, oxygen and nitrogen gas at 12.1 eV and 14.5 eV respectively. However, the shape of helium's Paschen curve is such that, at atmospheric pressure, the voltage required to initiate a discharge across two electrodes with a given gap distance is lower for helium than for argon, oxygen or nitrogen. This relationship between breakdown voltage and pressure for various gases can be seen in FIG. 4.

For example, if two electrodes are separated by 1 cm, the breakdown voltage at 760 Torr (atmospheric pressure) will be about 750 Volts for helium, 1100 Volts for argon and 2000 Volts for nitrogen. Note that these values assume parallel plates of infinite extent. In actual practice, sharp edges, surface asperities and roughness, and so on can somewhat reduce these values. Also, a discharge may modify the surface so that the actual breakdown voltage of a subsequent discharge is also somewhat different than the previous discharge. Consequently, a number of test results are averaged to obtain a consistent breakdown voltage value, for a given gap, pressure and gas composition.

This property of differential breakdown voltage of different gases is used to provide a means of discriminating between these gases. If a periodic waveform is applied to the two electrodes in the above example, the time from the zero-crossing to the initiation of the discharge can be used to discriminate among various gases. An example of a linear ramp voltage is shown in FIG. 5.

Figure 5:
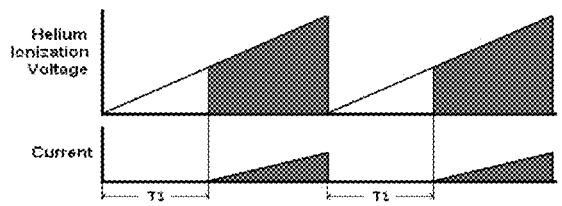
FIG. 5 is an illustration of differential breakdown voltage timing for helium and argon.
Figure 5:
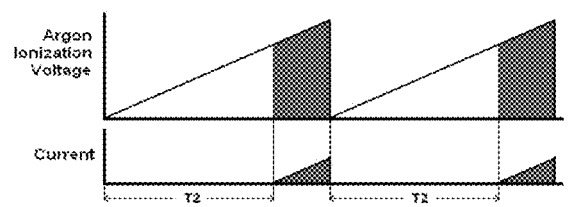

The time T1 in FIG. 5 is the duration between the zero-crossing and the breakdown voltage for helium, and T2 is for argon. Since a higher breakdown voltage is needed for argon, it takes longer for the linear ramp periodic waveform to reach that voltage and so T1 is less than T2.

Once a breakdown voltage is reached, however, self-ionization processes in the discharge allow the voltage to be reduced considerably before the discharge extinguishes. This is illustrated in FIG. 6 where a current-limited sine wave periodic waveform is used.

Figure 6:
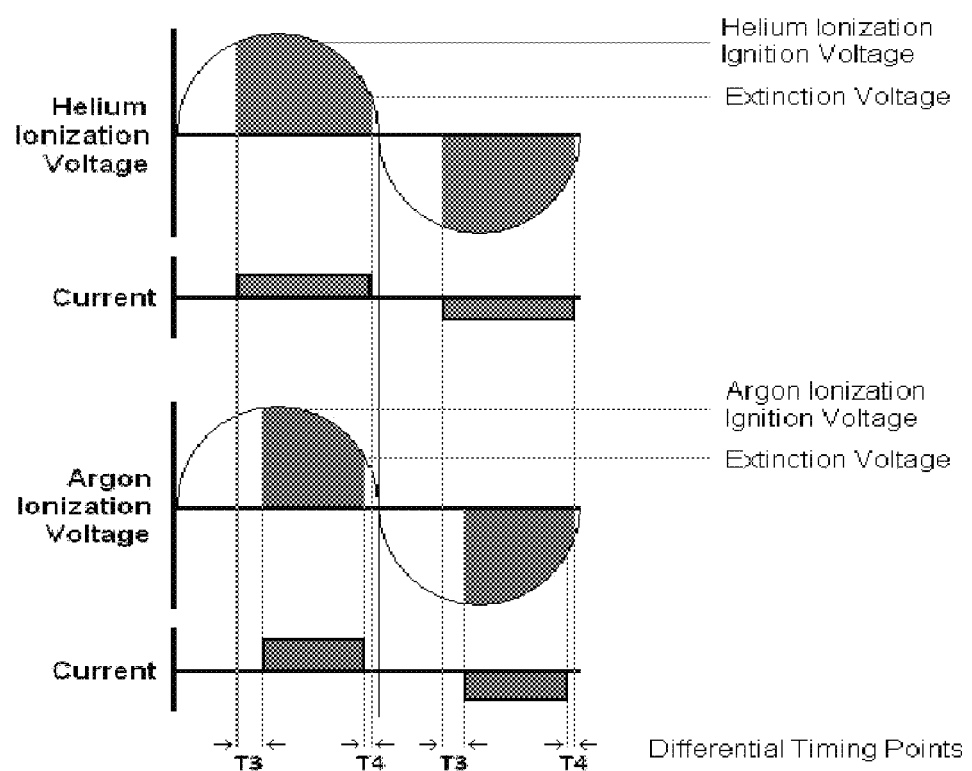
FIG. 6 is an illustration of differential breakdown voltages for helium and argon using a sine wave.

In FIG. 6, the differential timing T3 shows the difference in breakdown timing between helium and argon and T4 shows the discharge extinction timing difference for each half cycle of a sine wave. Note that the current in this example is limited so that it simply shows an on/off waveform.

Figure 7:
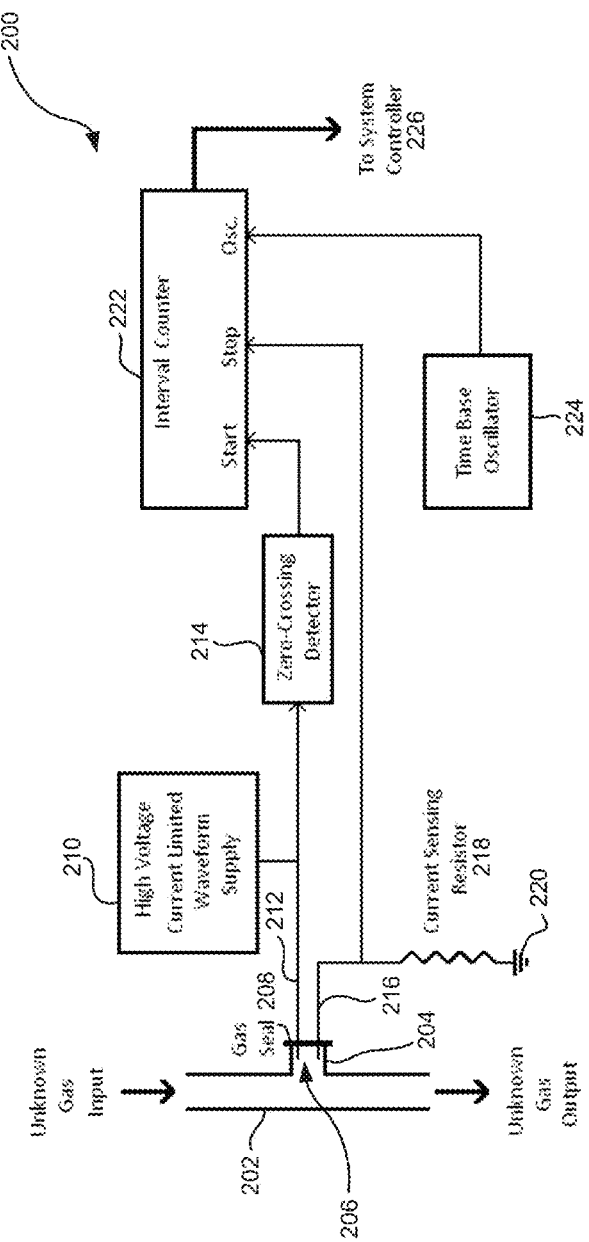
FIG. 7 is a diagram of a gas discrimination system employing ionization discharge timing in accordance with an embodiment of the present disclosure.

This variation in the timing of the onset of breakdown voltage using a periodic waveform allows the discrimination of different gas compositions. A diagram of a system 200 using this approach is shown in FIG. 7. An unknown gas flows through a tube 202 with a side port 204 containing two test electrodes 206 that are mounted in an electrically insulating gas seal 208. A high voltage current-limited waveform supply 210 is connected to one 212 of the test electrodes and also to a zero-crossing detector 214. The other test electrode 216 is connected to a current sensing resistor 218 which is then connected to ground 220.

When the high voltage waveform supply goes above (or below) zero volts, the zero-crossing detector 214 initiates an interval counter 222. This counter 222 continues to increment counts, at a rate determined by a time base oscillator 224, until the unknown gas discharges. When this occurs, the discharge current is sensed by the current sensing resistor 218. This resistor value is selected so that the anticipated nominal discharge current will produce a sufficient voltage drop across the resistor 218 that it can be recognized as a logic level voltage. For example, if the nominal discharge current is set to 1 milliampere and a 5 volt logic level signal is required, then the value of resistor 218 would be 5 kilohms. Note that the discharge current is set by the high voltage current limited waveform supply 210, and this discharge current value will be independent of which gas (helium or argon) is being detected. Also, if a bipolar high voltage waveform is used, as is shown in FIG. 6, a polarity-maintaining component, such as a full wave diode bridge (not shown) would be needed between resistor 218 and interval counter 222 to be certain this logic level is always positive.

Once the discharge occurs, the logic level voltage from resistor 218 signals the interval counter 222 to stop and transfer the final count value from the interval counter 222 to a system controller 226. The final count value would then be directly proportional to the breakdown voltage. The interval counter 222 is then reset and the process is repeated.

Since there may be some discharge to discharge variation in the timing signature, several tests may be made and averaged to overcome timing "jitter". The averaged final count value is then compared to a predetermined value to produce a "Go/No-Go" signal for the expected gas.

III. Discrimination by Emission Spectra:

When an ionized gas re-captures an electron, it emits light at characteristic wavelengths, known as its emission spectrum. Some of the stronger emission line wavelengths (in nm) for helium and argon are listed below in Table 1. Note that since helium has only two electrons, its spectrum is relatively simple, while argon, with 18 electrons and associated orbital structure, has a more complex spectrum.

TABLE 1

Some of the stronger emission lines (in nm) for helium and argon.

| Helium | Argon | |
|---|---|---|
| 667.8 | 694.5 | 603.2 |
| 587.6 | 687.1 | 560.7 |
| 501.6 | 675.3 | 426.6 |
| 492.2 | 668.4 | 419.8 |
| 447.2 | 641.6 | 416.4 |

Optical band-pass interference filters are readily available with Full Width Half Maximum (FWHM) of 10 nm. As seen above, some regions of emissions spectra are relatively congested, particularly in the upper 600's nm, and would require a narrower FWHM to be able to uniquely identify a particular emission line.

Two approaches are outlined for discrimination of argon and helium by their emission spectra. In the first approach, a specific emission line is sought. For example, the 501.6 nm line for helium and the 560.7 nm line for argon could be used to determine if either of these gases are present. This approach is illustrated in FIG. 8.

Figure 8:
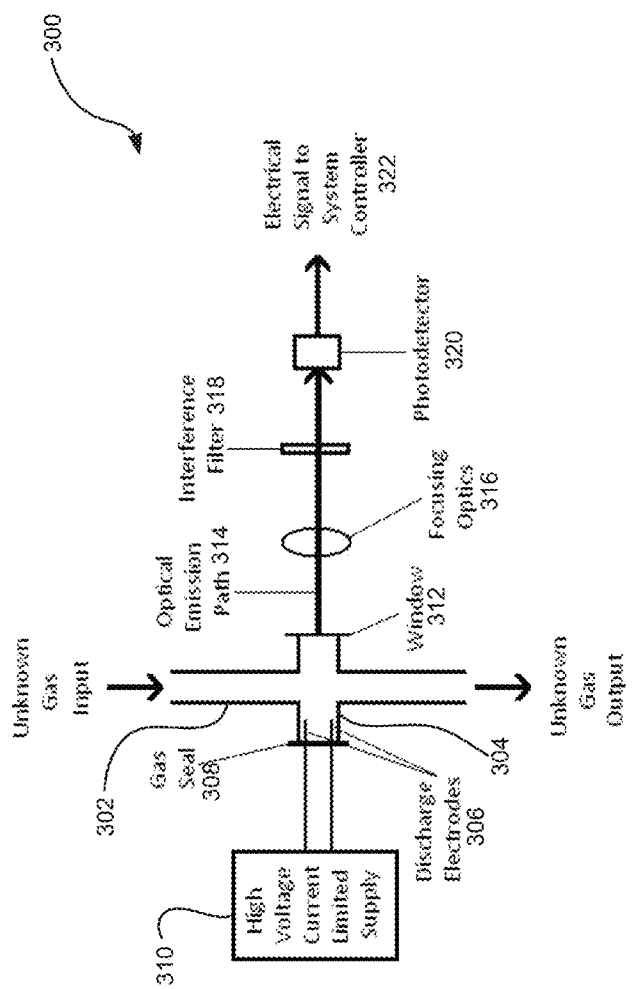
FIG. 8 is a diagram of a gas discrimination system employing single band pass emission spectrum discrimination in accordance with an embodiment of the present disclosure.

Referring to FIG. 8, a diagram of a system 300 using single band pass emission spectrum discrimination is shown. An unknown gas flows through a tube 302 with a side port 304 containing two discharge electrodes 306 that are mounted in an electrically insulating gas seal 308. A high voltage current-limited waveform supply 310 is connected to the discharge electrodes 306.

A discharge will occur between electrodes 306, whose emission spectrum light passes through window 312 along optical emission path 314 and through focusing optics 316. Interference filter 318 selects a narrow range of wavelengths in which the expected emission line for an expected gas would lie. If this gas is present, its emission line light would pass through interference filter 318 and be detected by photodetector 320. The detected signal from photodetector 320 is then sent to a system controller 322 to produce a "Go/No-Go" signal for the expected gas.

A more flexible approach would be to split the optical emission into two paths with a beam splitter to permit simultaneous detection of two wavelengths. This process of splitting the beam can be continued additional times to monitor more wavelengths, within the limiting sensitivity of the photodetectors. This approach is illustrated in FIG. 9.

Figure 9:
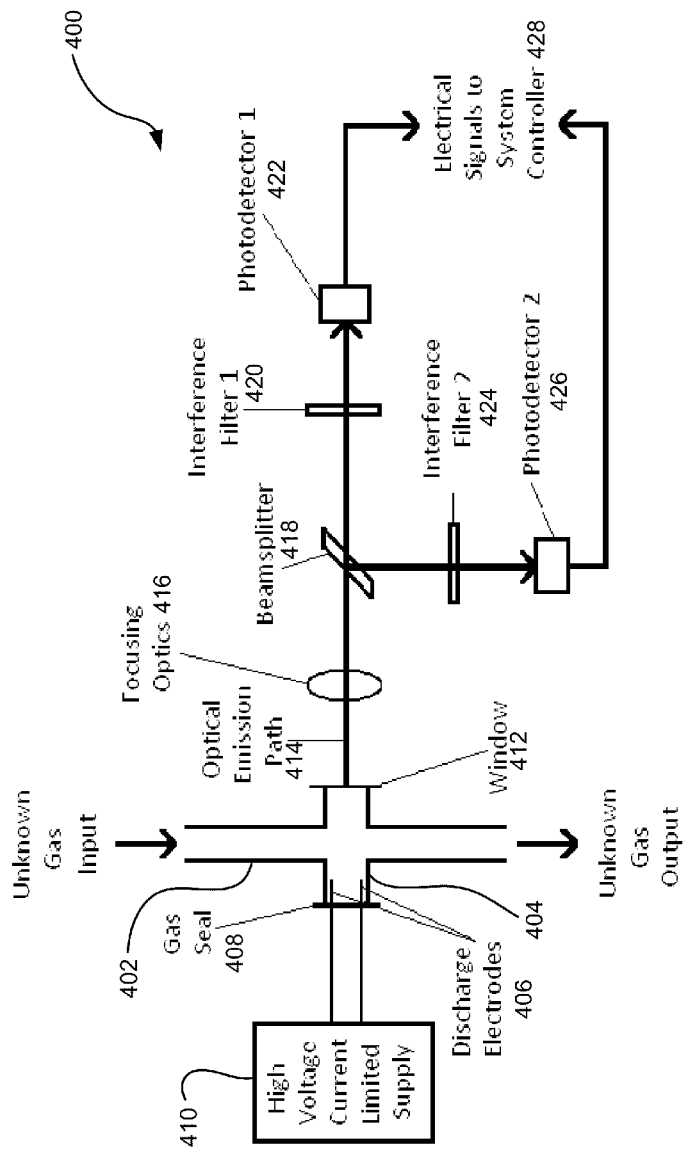
FIG. 9 is a diagram of a gas discrimination system employing dual band pass emission spectrum discrimination in accordance with an embodiment of the present disclosure.

Referring to FIG. 9, a diagram of a system 400 using dual band pass emission spectrum discrimination is shown. An unknown gas flows through a tube 402 with a side port 404 containing two discharge electrodes 406 that are mounted in an electrically insulating gas seal 408. A high voltage current-limited waveform supply 410 is connected to the discharge electrodes 406.

A discharge will occur between electrodes 406, whose emission spectrum light passes through window 412 along optical emission path 414 and through focusing optics 416. Beamsplitter 418 divides the emission spectrum light into two paths so that half of the emission spectrum light is presented to interference filter 420 and photodetector 422, and the other half to interference filter 424 and photodetector 426. Emission spectral components that are present and can pass through interference filter 420 and/or 424 will be detected by photodetectors 422 and/or 426 respectively, and be used by system controller 428 to produce a "Go/No-Go" signal for the expected gas.

The approach illustrated in FIG. 8 would be useful in the detection of only one gas, ideally exclusively of all others, while the approach in FIG. 9 has the capability of detecting two gases, either helium or argon, for example. It would then be possible, in the event of misconnected helium and argon gas lines, to either indicate the problem with an alarm and inhibit system operation, or alternatively, provide a cross-over solenoid valve network that would reroute the misconnected gases to their proper internal system feed lines automatically, for example, the cross-over network as shown in FIG. 2.

Situations may arise, for example in the use of mixed gases such as helium with oxygen that single emission line detection is insufficient to discriminate among various gases. In this case, the approach in FIG. 9 can use two (or more) simultaneous emission lines of the same gas. However, now only a single gas can be detected as was the case in the approach of FIG. 8.

IV. Discrimination by Differential Velocity of Propagation:

While the absorption of ultrasonic frequencies is strong in helium, the absorption at audio frequencies, from 20 Hz to 20 kHz, is much weaker, and may be difficult to use to discriminate between helium and argon or air at these frequencies. Instead, the differential velocity of propagation between these gases can be used, and its effect on resonance conditions, phase differences, and time-of-flight to discriminate between them.

Among the exceptional properties of helium is its high velocity of propagation, 965 meters per second, as compared to 331 m/s for air and 319 m/s for argon, all measured at 0° C. The velocity of propagation can be written as the product of the wavelength and frequency:

$$v = \lambda f \qquad (1)$$

where v is the velocity of propagation, $\lambda$ is the wavelength, and f is the frequency. This equation can be written in terms of wavelength as:

$$\lambda = v/f \qquad (2)$$

In other words, as the velocity of propagation increases, the wavelength increases proportionally for a given fixed frequency.

An acoustical resonance condition can be made to exist when the distance between two surfaces, L, is an integer multiple of half the wavelength:

$$L = n(\lambda/2) \quad (3)$$

where n is an integer.

Since the wavelength depends on the velocity of propagation for a given frequency, a structure that is in resonance for a specific velocity of propagation will not be in resonance for a different velocity of propagation, either higher or lower. This property can be employed to construct a structure that is in resonance only for helium so that when any gas with a different velocity of propagation is used, the resonance condition ceases.

Figure 10:
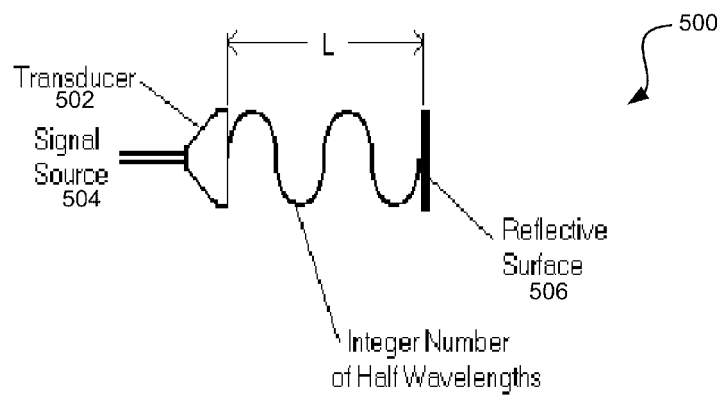
FIG. 10 is an illustration of a resonant condition between a transducer and a reflective surface.
Figure 11:
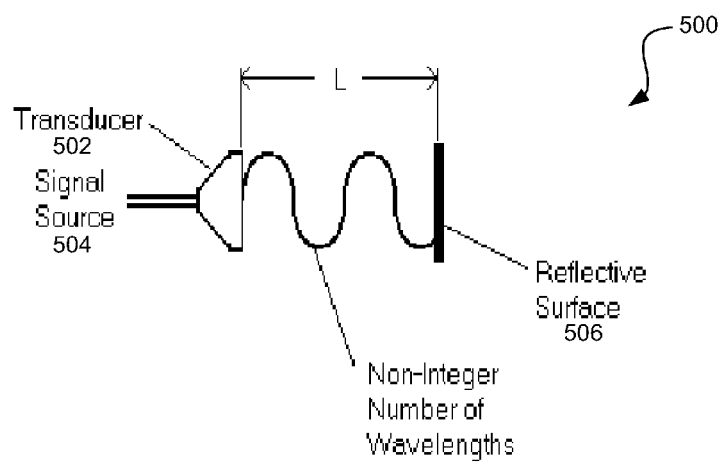
FIG. 11 is an illustration of a non-resonant condition between a transducer and a reflective surface.

These structures can take several forms, but all will require at least one transducer to introduce the acoustical waves into the structure. If a reflective surface is placed opposite the transducer at a distance L that satisfies equation 3 above, a resonance condition can develop. That is, assuming the transducer and signal source operate at a fixed frequency, when different gases are introduced between the transducer and reflective surface, the wavelength of the sound will be different, either establishing or preventing a resonance condition. This is illustrated in FIG. 10, which shows a resonance condition, where transducer 502, fed by a signal source 504, is disposed a distance L from reflective surface 506. In contrast, FIG. 11 illustrates when the structure 500 is out of resonance.

Figure 12:
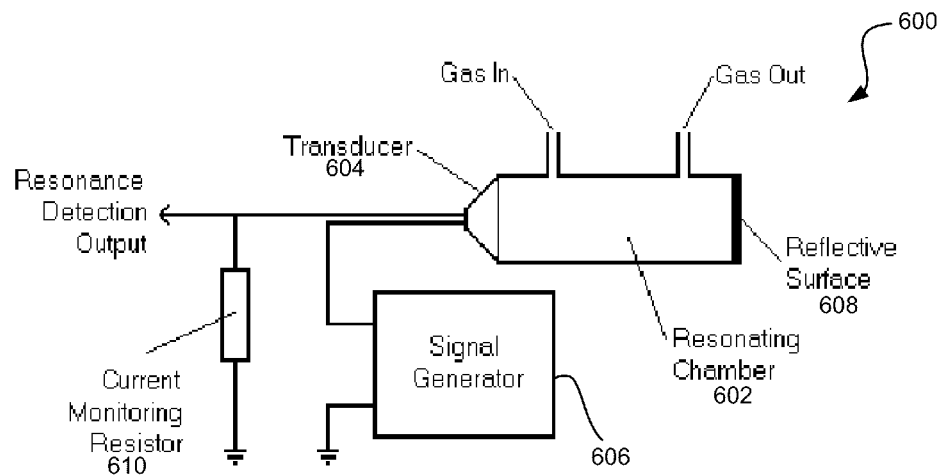
FIG. 12 is a diagram of a gas discrimination system employing a single transducer resonator with a reflective surface in accordance with an embodiment of the present disclosure.

FIG. 12 illustrates one embodiment of a gas discriminator 600 in accordance with the present disclosure, where the gas in question is admitted into the resonating chamber 602 and a transducer 604 launches acoustical waves into the resonating chamber 602. A resonant condition can be made to exist, which will depend on the distance L, the velocity of propagation of the gas in the resonating chamber 602, and the acoustical frequency launched by the transducer 604, which is determined by the signal generator 606. It is to be appreciated that the distance L is the distance from the transducer 604 to the reflective surface 608 of the resonating chamber 602.

Figure 13:
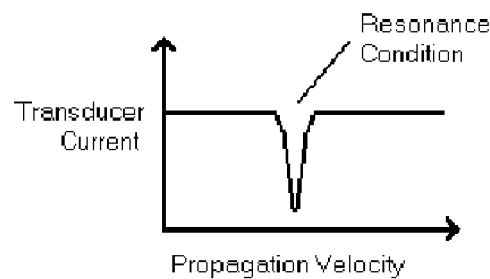
FIG. 13 is an illustration of a change in transducer current during resonance.

During resonance, acoustical waves reinforce each other, so the electrical energy required to create a given sound level significantly decreases. This is shown in FIG. 13. The amount of electrical energy to generate the acoustical waves is monitored by the current monitoring resistor 610 in FIG. 12. During resonance, the amount of current will decrease, assuming a fixed voltage level from the signal generator 606. Therefore, it is determined that when the current monitored by the current monitoring resistor 610 is below a predetermined threshold or setpoint, the structure is in resonance and, when current monitored by the current monitoring resistor 610 is above the predetermined threshold or setpoint, it is out of resonance. Based on the resonance or non-resonance condition detected, the gas discriminator 600 determines if the gas being used is of the proper type or not, via a processor, controller, logic or other similar means.

It is to be appreciated that the predetermined threshold or setpoint may be adjustable. The predetermined threshold or setpoint can be selected based on the gas to be identified. For example, a table correlating a setpoint based on gas type may be stored in a memory of the gas discriminator, or the electrosurgical generator 12, and selected based on the gas type entered by a user via the user interface portion 44 of the gas discriminator.

Figure 14:
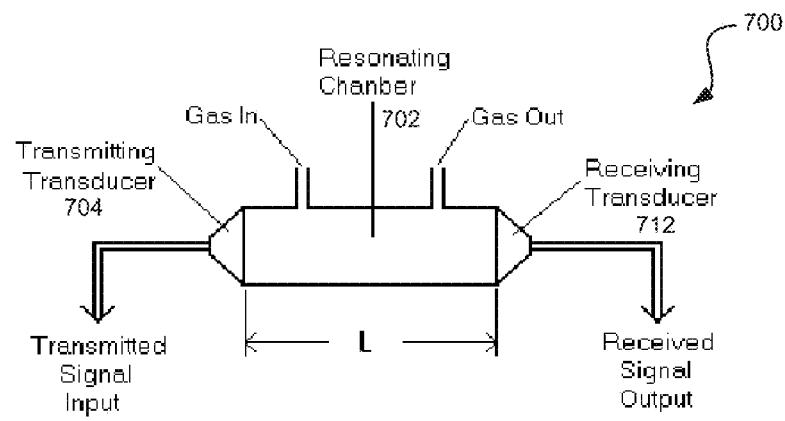
FIG. 14 is a diagram of a gas discrimination system employing a dual transducer resonator in accordance with an embodiment of the present disclosure.

In another embodiment, two transducers are used, as illustrated in the gas discriminator 700 shown in FIG. 14. Here, a resonant condition can be made to exist when the distance between the two transducers, L, satisfies equation 3 above. It is to be appreciated that distance L is the distance of the resonating chamber 702 between transmitting transducer 704 and receiving transducer 712. Acoustical waves launched by the first transducer, the transmitting transducer 704, will be detected by the second transducer, the receiving transducer 712. At resonance, the amplitude of sound waves detected by the receiving transducer 712 will increase significantly. Since the resonant condition, for a given distance L, will depend on the velocity of propagation, the structure 700 in FIG. 14 can be tuned by varying L so that it is in resonance only for helium gas at a given frequency. Conversely, it can be tuned so that it is in resonance for another gas, and out of resonance when helium is present. Alternately, L can be fixed and the frequency varied until resonance is achieved.

In another embodiment, the frequency of the transmitting transducer is modulated, or periodically swept over a range of frequencies. For a given velocity of propagation, a resonant condition will occur at a specific frequency for a given value of L. So for different gases with different velocities of propagation, a different resonant frequency could be used to identify, or exclude identity, of that gas. Note that this concept, illustrated in FIG. 15, is also applicable to the single transducer embodiment in FIG. 12.

Figure 15:
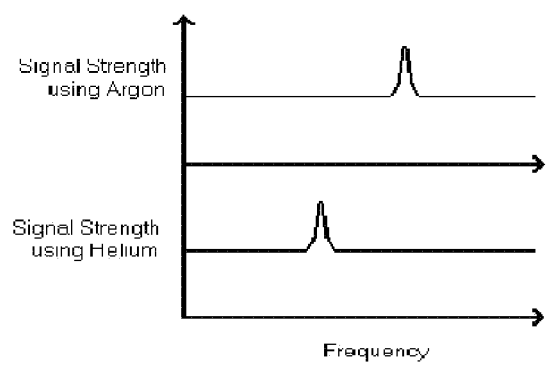
FIG. 15 is an illustration of resonant conditions with sweeping frequencies for different gases.

It can be seen in FIG. 15 that because helium will have a longer wavelength at a given frequency, as compared to argon at the same frequency, the resonant condition will occur sooner in the sweep of frequencies for helium than for argon. In use, a timer would be initiated at the start of the frequency sweep and stopped when the resonance condition is detected. The value of this timer would be compared to previously determined values for different gases with significantly different velocities of propagation, and then be used to identify whether a particular gas is present or absent.

It is to be appreciated that the resonant chamber will have multiple resonant frequencies (i.e. different values of n in equation 3). It is important that the range of swept frequencies not be so broad that it encompasses multiple values of n, or one value of n for one gas and a different value of n for a second gas.

Figure 16:
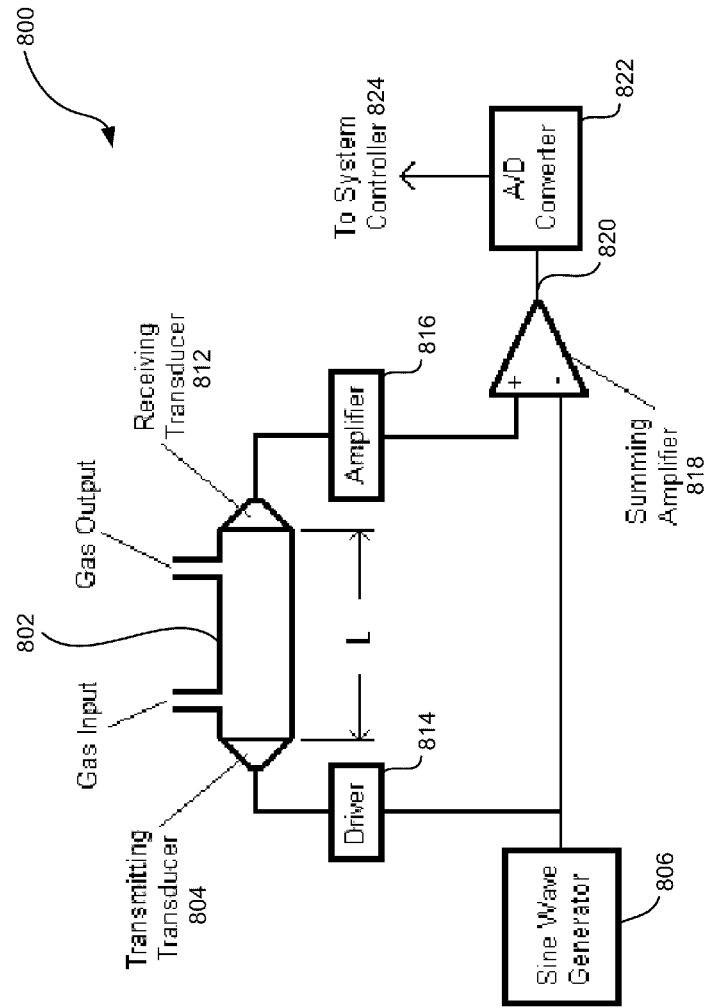
FIG. 16 is a diagram of a gas discrimination system employing wavelength-dependent phase difference discrimination in accordance with an embodiment of the present disclosure.

Since the velocity of propagation may be different for different gases, and so the associated wavelengths will be similarly different, the phase difference, measured at two fixed points along the path of propagation, will be different for different wavelengths. A system 800 for measuring the phase difference is shown in FIG. 16.

A sine wave generator 806 (although other waveforms could be used such as a triangular, sawtooth, etc.) feeds a driver 814 which launches acoustical waves with a transmitting transducer 804. After traveling distance L, the acoustical waves are received by the receiving transducer 812, fed to an amplifier 816, and then compared in a summing amplifier 818. While several different combinations are possible, the simplest case is where the amplitudes of the two signals presented to the inputs of the summing amplifier 818 are the same, and the summing amplifier 818 itself has a gain of 1, producing a simple summation output 820. This output 820 is then fed to an analog-to-digital (A/D) converter 822, whose digital output is read by a system controller 824. The A/D converter's digital output "signature" is compared to a previously stored one and a determination is made regarding which gas is being tested.

The summation of two sine waves of equal amplitudes is relatively straightforward and only depends on the phase difference between them. For example, if the distance L in FIG. 16 is chosen to be one full wavelength (or an integer multiple), the waves add to produce another sine wave of twice the amplitude. Similarly, if the L is a half wavelength, the two waves cancel and the output is zero. For waveforms other than a sine wave, the analysis is somewhat more complicated. One approach is to chose a distance L and feed in a test gas and note the resulting digital "fingerprint" produced by the A/D converter for a given frequency. This fingerprint is stored and used later as a comparison reference.

While the foregoing considered the effect of different velocities of propagation of different gases on their wavelengths and associated resonances, these different velocities will also affect the propagation time of a pulse wavefront. The higher the velocity of propagation, the less time it will take a pulse wavefront to pass between two fixed points. For example, with helium, which has a velocity of propagation of 965 meters/second, a pulse wavefront will take approximately 1.036 milliseconds to travel one meter, or about 10.36 microseconds to travel one centimeter. Similarly, for air, about 30.21 microseconds are required to travel one centimeter, and about 31.35 microseconds for argon, all when measured at 0° C. The "time-of-flight" for a wavefront to pass between two fixed points would be given by:

$$t = L/v \quad (4)$$

where t is the time-of-flight between two points that are distance L apart, given a velocity of propagation of v. A system 900 to measure the time-of-flight is illustrated in FIG. 17.

Figure 17:
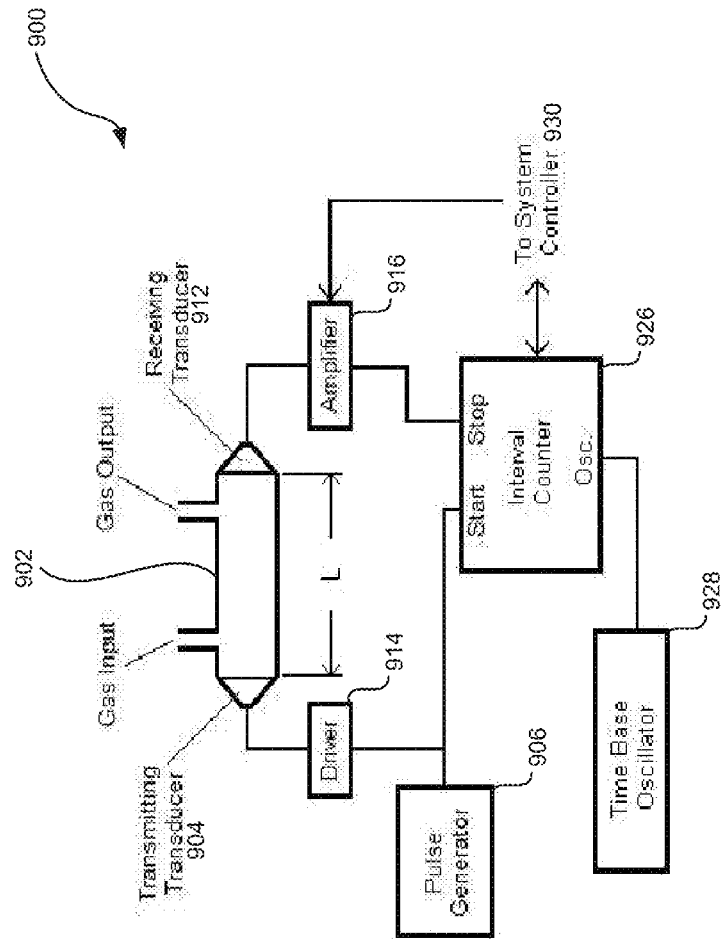
FIG. 17 is a diagram of a gas discrimination system employing time-of-flight measurement discrimination in accordance with an embodiment of the present disclosure.

Referring to the gas discriminator 900 in FIG. 17, a repetitive pulse from a pulse generator 906 is fed to a driver 914 and is then applied to the transmitting transducer 904. The pulse duration is sufficient to produce a detectable acoustical wavefront at the receiving transducer 912 after it has passed through an amplifier 916. The pulse repetition rate is sufficiently low that multiple reflections and reverberations of the initial acoustical wavefront have had time to decay away. At the onset of the transmitted pulse, an interval counter 926 is started, and it is stopped when the receiving transducer 912 detects the pulse wavefront. The value of the interval counter 926, whose counting rate is determined by the time base oscillator 928, is proportional to the transit time of the wavefront between the transmitting transducer 904 and receiving transducer 912, and therefore, the distance L, as related by equation 4 above. This value is then transferred to the system controller 930. This system controller 930 resets the counter 926 for the next pulse measurement, and then compares the measured value of the transit time to a preset value and determines if the gas is or is not the gas being tested for. In addition, the system controller 930 may gate the amplifier 916 (turn it on or off) to minimize the effects of noise. This noise may be electrical, or acoustical, which is generated by the flow turbulence of the gas being tested. The amplifier 916 would be gated on only when the received pulse is anticipated to arrive.

Additional methods may be employed to reduce flow turbulence noise, including a flow-laminarizing element consisting of a bundle of small tubes or a series of plates with many holes, to "straighten" an otherwise turbulent flow. Also, flow turbulence noise can be reduced by sampling a small fraction of the total gas flow and passing that through the test chamber through a bypass arrangement so that the net flow through the test chamber is reduced.

Figure 18:
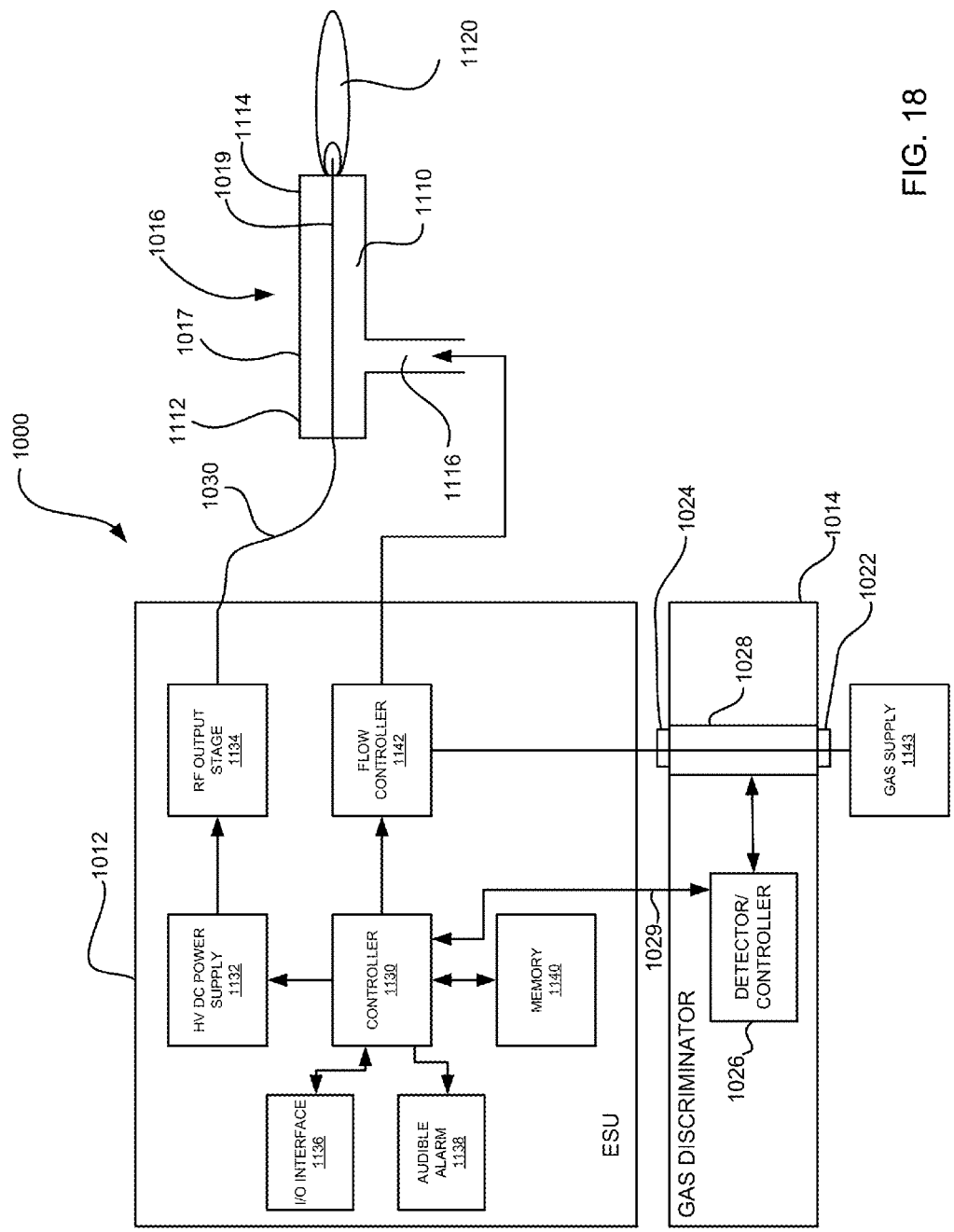
FIG. 18 illustrates an electrosurgical system in accordance with an embodiment of the present disclosure.

Referring to FIG. 18, an electrosurgical system 1000 is illustrated including an electrosurgical generator (ESU) 1012, a gas discriminator 1014 and an electrosurgical handpiece 1016, e.g., a plasma generator. The gas discriminator 1014 shown in FIG. 18 may be any of the above-described embodiments of a gas discriminator or any combination thereof. As shown in FIG. 18, the gas discriminator 1014 generally includes a gas input 1022, a gas output 1024 and a detector/controller 1026 coupled to a tube or chamber 1028 for detected a type of gas flowing therethrough. As described above, the detector/controller 1026 provides an output control signal 1029, for example, indicative of the gas type, a GO signal, No Go signal, etc. In this example, the output control signal 1029 is transmitted to the electrosurgical generator 1012.

The electrosurgical generator 1012 includes a controller 1130 that controls a HV DC power supply 1132 (which receives power from an external source) to supply electrosurgical energy being output from an RF output stage 1134 via at least one conductor 1030 to the handpiece 1016. The electrosurgical generator 1012 will indicate various operating conditions to an operator via an I/O interface 136 such as the input section 20, level controls 22 and indicators 24 as shown in FIG. 1. The electrosurgical generator 1012 may further includes an audible alarm 1138 to alert an operator to various conditions.

The electrosurgical handpiece 1016 includes an electrode 1019 supported by the handpiece and at least partially disposed in a fluid flow housing 1017. The electrode 1019 is concentrically disposed within an inner noble gas conduit 1110 having a proximal end 1112 and a distal end 1114 coupled to a noble gas source 1143 by a noble gas supply conduit 1116 to feed a noble gas such as helium or argon to the noble gas conduit 1110. A conducting plasma stream 1120 generated by the handpiece 1016 couples the electrosurgical generator 1012 to a patient, e.g., a surgical site, tissue, etc.

The electrosurgical generator 1012 further includes a flow controller 142 for controlling the flow of gas to the electrosurgical handpiece 1016. The flow controller 1142 is coupled to the controller 1130 and receives control signals from the controller 1130 based on user input via I/O interface 1136 or based on an algorithm or software function stored in memory 1140. In one embodiment, the flow controller 1142 may receive a control signal from the controller 1130 based on a second control signal, e.g., signal 1029, received at the controller 1130 from the gas discriminator 1014. For example, if the gas discriminator 1014 determines that an expected gas is fed into the gas discriminator 1014 and/or handpiece 1016, the gas discriminator 1016 transmits a "Go" signal to the controller 1130 which subsequently enables the flow controller 1142 and enables the RF output stage 1134. Alternatively, if the gas discriminator 1014 determines that the gas fed into the gas discriminator 1014 and/or handpiece 1016 is a gas other than the expected gas, the gas discriminator 1016 transmits a "No Go" signal to the controller 1130 which subsequently disables the flow controller 1142 and disables the RF output stage 1134. It is to be appreciated that the control signal 1029 may simply cause the electrosurgical generator to shutdown the RF output stage 1134 in certain embodiments where a flow controller 1142 is not provided. It is to be further appreciated that the control signal 1029 generated by the gas discriminator 1014 may be coupled to the handpiece 1016 to disable the handpiece when necessary. Other methods to disable or stop an electrosurgical procedure, device or apparatus via the output of the gas discriminator are contemplated to be within the scope of the present disclosure.

Although in the embodiment shown, the flow controller 1142 is disposed in the electrosurgical generator 1012, the flow controller 1142 can be located external to the electrosurgical generator 1012 and disposed, for example, in a separate housing, in the handpiece 1016, in the gas discriminator 1014, etc. Additionally, although in the embodiment shown, the gas discriminator 1014 is illustrated as a separate unit in an external housing, the gas discriminator 1014 may be disposed in the electrosurgical generator 1012 under a single housing or enclosure or in the handpiece 1016.

It is to be appreciated that the systems and methods of the present disclosure may be employed where mixtures of gases are used, for example, a blend of both helium and argon, or helium containing oxygen, or other gas combinations. In one embodiment, the gas discriminating systems of the present disclosure produces an internal test result signal that is associated with a specific gas combination ratio that is stored for subsequent comparisons. A plurality of tests may be conducted to generate a database or look-up table for various combinations of different gases and for various ratios of different gases. The database or look-up table may then be stored in a memory, e.g., memory 1140 in the electrosurgical generator 1012. These internal test result signals can then be compared, e.g., by controller 1130, to a measured value as determined by any of the gas discriminators described above and a "Go/No Go" signal is then issued if the expected gas combination is present or not. Alternatively, the controller 1130 may scan all the values stored in the database and look-up to determine which types of gas or combination of gas types was input to the system.

The systems and methods of the present disclosure may also be employed to verify the purity of the gas used. As above, in one embodiment, the gas discriminating systems of the present disclosure produces an internal test result signal that is associated with a predetermined purity level for a specific gas type that is stored for subsequent comparisons. A plurality of tests may be conducted to generate a database or look-up table for various purity levels of different gases. The database or look-up table may then be stored in a memory, e.g., memory 1140 in the electrosurgical generator 1012. These internal test result signals can then be compared, e.g., by controller 1130, to a measured value as determined by any of the gas discriminators described above and issue a "Go/No Go" if the gas has an acceptable purity level, or not. Alternatively, the controller 1130 may scan all the values stored in the database and look-up to determine the purity level for the type of gas that was input to the system.

It will be appreciated by those skilled in the art that the block diagrams presented herein represent conceptual views of illustrative circuitry embodying the principles of the disclosure. Similarly, it will be appreciated that any flow charts, flow diagrams, state transition diagrams, pseudo-code, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor ("DSP") hardware, read only memory ("ROM") for storing software, random access memory ("RAM"), and nonvolatile storage.

Other hardware, conventional and/or custom, may also be included. Similarly, any switches shown in the figures are conceptual only. Their function may be carried out through the operation of program logic, through dedicated logic, through the interaction of program control and dedicated logic, or even manually, the particular technique being selectable by the implementer as more specifically understood from the context.

It is to be appreciated that the various features shown and described are interchangeable, that is a feature shown in one embodiment may be incorporated into another embodiment.

While the disclosure has been shown and described with reference to certain preferred embodiments thereof, it will be understood by those skilled in the art that various changes in form and detail may be made therein without departing from the spirit and scope of the disclosure.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

What is claimed is:

1. An apparatus for use with a medical device comprising:
   at least one gas input configured to receive a gas;
   an acoustic absorption type gas discriminator coupled to the at least one gas input and configured to determine a type of the received gas, the acoustic absorption type gas discriminator further configured to generate a signal indicative of the received gas type; and
   a controller configured to receive the received gas type signal, compare the received gas type to an expected gas type and generate a control signal to enable or disable the medical device based on the comparison,
   wherein the expected gas type is a combination of at least two different types of gas.

2. The apparatus as in claim 1, wherein the medical device is an electrosurgical generator.

3. The apparatus as in claim 1, wherein the medical device is an electrosurgical handpiece.

4. The apparatus as in claim 1, further comprising at least one gas output configured to supply the inputted gas to an electrosurgical handpiece.

5. The apparatus as in claim 4, further comprising a user interface configured for inputting to the controller the expected gas type.

6. The apparatus as in claim 1, wherein the at least two different types of gas include helium and argon.

7. The apparatus as in claim 1, wherein the at least two different types of gas include helium and oxygen.

8. The apparatus as in claim 1, further comprising a non-transitory memory coupled to the controller, wherein the non-transitory memory stores a database including signal values for combinations of the at least two different types of gas.

9. The apparatus as in claim 8, wherein the controller scans the signal values of the database to determine the received gas type based on the received gas type signal.

10. The apparatus as in claim 9, further comprising a user interface that indicates the determined received gas type.

11. The apparatus as in claim 1, further comprising a non-transitory memory coupled to the controller, wherein the non-transitory memory stores a database including signal values for ratio combinations of the at least two different types of gas.

12. The apparatus as in claim 11, wherein the controller scans the signal values of the database to determine the ratio combination of the at least two different types of gas based on the received gas type signal.

13. The apparatus as in claim 12, further comprising a user interface that indicates the determined ratio combination of the at least two different types of gas.

* * * * *